US012678116B2

(12) United States Patent
Hugg et al.

(10) Patent No.: US 12,678,116 B2
(45) Date of Patent: *Jul. 14, 2026

(54) COMPUTER ASSISTED MOLECULAR IMAGING METHODS AND SYSTEMS

(71) Applicant: Smart Breast Corporation, Sherman Oaks, CA (US)

(72) Inventors: James W. Hugg, Tyler, TX (US); Bradley E. Patt, Sherman Oaks, CA (US)

(73) Assignee: SMART BREAST CORPORATION, Sherman Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/266,337

(22) Filed: Jul. 11, 2025

(65) Prior Publication Data

US 2025/0339117 A1     Nov. 6, 2025

Related U.S. Application Data

(63) Continuation of application No. 18/751,222, filed on Jun. 22, 2024, now Pat. No. 12,357,256.

(Continued)

(51) Int. Cl.
*A61B 6/50*          (2024.01)
*A61B 6/03*          (2006.01)
(Continued)

(52) U.S. Cl.
CPC ............. *A61B 6/502* (2013.01); *A61B 6/037* (2013.01); *A61B 6/12* (2013.01); *A61B 6/4291* (2013.01);
(Continued)

(58) Field of Classification Search
CPC ...... G16H 50/20; A61B 6/502; A61B 6/0414; G06T 7/0012; G06T 2207/30068; G06T 2207/30096
See application file for complete search history.

(56) References Cited

U.S. PATENT DOCUMENTS

| | | | |
|---|---|---|---|
| 6,377,838 B1 | 4/2002 | Iwanczyk | |
| 10,617,382 B2 * | 4/2020 | Hugg | A61B 6/502 |

(Continued)

OTHER PUBLICATIONS

Moja, L. et. al. "Effectiveness of computerized decision support systems linked to electronic health records: a systematic review and meta-analysis". American Journal of Public Health, Dec. 2014, vol. 104, No. 12, p. e12-e22.

(Continued)

*Primary Examiner* — Bobbak Safaipour
(74) *Attorney, Agent, or Firm* — BARTONY & ASSOCIATES, LLC

(57)          ABSTRACT

A method for molecular image acquisition includes beginning acquisition of a molecular image via a molecular imaging system, performing one or more analyses of the molecular image during acquisition of the molecular image to determine whether at least one lesion is present in the image, and if it is determined that there is either at least one lesion present or there is not at least one lesion present in the image in any one of the one or more analyses of the molecular image, performing at least one of providing a recommendation that the acquisition be stopped or stopping the acquisition automatically.

21 Claims, 9 Drawing Sheets

Related U.S. Application Data

(60) Provisional application No. 63/522,890, filed on Jun. 23, 2023.

(51) Int. Cl.

| | |
|---|---|
| *A61B 6/12* | (2006.01) |
| *A61B 6/42* | (2024.01) |
| *G06T 7/00* | (2017.01) |
| *G16H 50/20* | (2018.01) |
| *A61B 6/04* | (2006.01) |
| *A61B 10/00* | (2006.01) |

(52) U.S. Cl.
CPC ........... *G06T 7/0012* (2013.01); *G16H 50/20* (2018.01); *A61B 6/0414* (2013.01); *A61B 10/0041* (2013.01); *G06T 2207/30068* (2013.01); *G06T 2207/30096* (2013.01)

(56) References Cited

U.S. PATENT DOCUMENTS

| | | | | |
|---|---|---|---|---|
| 10,937,208 | B2 * | 3/2021 | Zhu | G06T 12/20 |
| 12,357,256 | B2 * | 7/2025 | Hugg | A61B 6/037 |
| 2018/0000461 | A1 * | 1/2018 | Venkataramani | A61B 5/4312 |
| 2018/0260949 | A1 * | 9/2018 | Kreeger | G06T 7/0016 |
| 2019/0076110 | A1 * | 3/2019 | Moriyasu | A61B 6/545 |
| 2020/0352537 | A1 * | 11/2020 | Bai | A61B 6/5235 |
| 2022/0338805 | A1 * | 10/2022 | Jeraj | A61B 5/4842 |
| 2024/0008839 | A1 * | 1/2024 | Yoo | A61B 5/015 |
| 2024/0116987 | A1 * | 4/2024 | Sonveaux | C12Y 101/01027 |

OTHER PUBLICATIONS

Singh, S., et. al., "Current Methods in Medical Image Segmentation, A Review," International Conference on Communications, Computing and Systems, p. 199-203 (2014).

Hosny, A. et. al. "Artificial intelligence in radiology", Nature Reviews Cancer, (2018) 18:500-510.

Mckinney, SM et al. "International evaluation of an AI system for breast cancer screening". Nature, (2020) 577:89-94.

Kobie, N. "DeepMind's new AI can spot breast cancer just as well as your doctor". Wired UK, (Jan. 1, 2020), 1-10.

Varghese, J et. al. "Effects of computerized decision support system implementations on patient outcomes in inpatient care: a systematic review". Journal of the American Medical Informatics Association, (2018) 25:593-602.

Pham, D.L. et. al., "A Survey Current Methods in Medical Image Segmentation," Annual Review of Biomedical Engineering, (2000) 2: 315-337.

Conners, A. L., et al, "Lexicon for standardized interpretation of gamma camera molecular breast imaging," Eur J Nucl Med Mol Imaging, 39:971-982 (2012).

Luca, Michael, et. al., Algorithms need Managers, Too, 2016, Harvard Business Review, pp. 96-101.

Conners, A. L., et al, Gamma Camera Breast Imaging Lexicon, American Roentgen Ray Society, AJR 2012; 199: W767-W774.

* cited by examiner

PRIOR ART

COMPUTER ASSISTED MOLECULAR IMAGING METHODS AND SYSTEMS

CROSS-REFERENCE TO RELATED APPLICATIONS

This application is a continuation patent application of U.S. patent application Ser. No. 18/751,222, filed Jun. 22, 2024, which claims benefit of U.S. Provisional Patent Application Ser. No. 63/522,890, filed Jun. 23, 2023, the disclosures of which are incorporated herein by reference.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

In 1990, the radiopharmaceutical imaging agent CARDIOLITE® (injectable Technetium Tc99m-Sestamibi) was cleared by the U.S. Food and Drug Administration (FDA) for Single-Photon Emission Computed Tomography (SPECT) myocardial perfusion imaging. As cardiologists gained experience with this mitochondrial tracer, they reported anecdotally that breast tumors also take up Sestamibi. This observation led to a new application in breast cancer detection named scintimammography, which generally involved imaging the patient with a whole-body gamma camera in a prone position with the breasts pendant or lightly compressed. Limitations of scintimammography were soon realized. In that regard, high radiation doses were required, and inadequate spatial resolution made the technique less effective for tumors smaller than one centimeter in diameter.

Techniques were then explored for using smaller gamma cameras dedicated to breast imaging. They can approach the breast more closely, so that spatial resolution can be improved, and smaller tumors detected. Both Positron Emission Tomography (PET) and planar Single-Photon Emission (SPE) imaging were developed and enjoyed some technical and commercial success. Radiation dose to the patient and technologist, however, remained too high for widespread use. In the early 2000's a new solid-state pixelated digital gamma photon detector became available for experimental applications. Working with the Mayo Clinic in Rochester, MN, both General Electric Healthcare and Gamma Medica developed cadmium-zinc-telluride (CdZnTe or CZT) gamma cameras for breast cancer imaging. The technique developed at the Mayo Clinic was named Molecular Breast Imaging (MBI), a term adopted now by most clinical users and all commercial vendors. In recent improvements, the whole-body radiation dose has been significantly reduced on some commercial systems so that it is nearly equivalent to that of screening mammography or digital breast tomosynthesis (DBT).

SUMMARY

In one aspect, a method for molecular image acquisition includes beginning acquisition of the molecular image via a molecular imaging system, performing one or more analyses of the molecular image during an image acquisition to determine with a predetermined statistical significance whether at least one hot spot is present in the image; and performing at least one of: (i) providing a recommendation that the image acquisition be stopped and (ii) stopping the image acquisition automatically. In a number of embodiments, a maximum duration or a maximum number of counts of the image acquisition is set at or before the beginning of the molecular image acquisition, and the method includes, after determining with the predetermined statistical significance whether at least one hot spot is present in the image, performing at least one of: (i) providing a recommendation that the acquisition be stopped before an end of the maximum duration or accumulation of the maximum number of counts of the image acquisition, and (ii) stopping the acquisition automatically before the end of the maximum duration or accumulation of the maximum number of counts of the image acquisition.

Performing the one or more analyses of the molecular image may include executing a software algorithm to characterize the image. The software algorithm may, for example, include one or more artificial intelligence algorithms. In a number of embodiments, the software algorithm includes at least one of a machine learning algorithm, a deep learning algorithm, a pattern recognition algorithm, an image segmentation algorithm, a signal-preserving noise filtering algorithm, or a count-density contouring algorithm.

The method may further include selecting a time during the image acquisition to initiate a first of the one or more analyses of the molecular image and a period of time between consecutive analyses. The molecular image may, for example, be created via molecular breast imaging (MBI), single photon emission (SPE) planar imaging, single photon emission computed tomography (SPECT), or positron emission tomography (PET).

The method may further include, after determining with the predetermined statistical significance whether at least one hot spot is present in the image, executing another software algorithm to measure at least one of (a) a characteristic of a background parenchyma and (b) a characteristic of the at least one hot spot and to assess a diagnostic significance of the at least one hot spot. The characteristic of the background parenchyma may be a standardized uptake value of the background parenchyma. The characteristic of the at least one hot spot may be selected from the group of a standardized uptake value of the at least one hot spot, a size of the at least one hot spot, or a location of the at least one spot.

In another aspect, a method for clinical decision support includes analyzing a molecular image to determine with a predetermined statistical significance whether at least one hot spot is present in the molecular image; and executing a software algorithm to measure a characteristic of at least one of (i) a background parenchyma of the molecular image and (ii) the at least one hot spot, and to assess a diagnostic significance of the at least one hot spot. In a number of embodiments, the characteristic of the background parenchyma is a standardized uptake value of the background parenchyma. In a number of embodiments, the characteristic of the at least one hot spot is selected from the group consisting of a standardized uptake value of the at least one hot spot, a size of the at least one hot spot, or a location of the at least one hot spot.

In another aspect, a system includes a memory system storing a software algorithm, and a processor system in operative connection with the memory system to execute the software algorithm. The system may be in communicative connection with a molecular imaging system to receive data of image acquisition from the molecular imaging system.

The software algorithm is configured (i) to perform one or more analyses of a molecular image during acquisition of the molecular image via a molecular imaging system and during the image acquisition, (ii) to determine with a predetermined statistical significance whether at least one hot spot is present in the molecular image, and (iii) to subsequently perform at least one of (a) providing a recommendation that the image acquisition be stopped, and (b) stopping the image acquisition automatically. In a number of embodiments, a maximum duration or a maximum number of counts of the image acquisition is set at or before the beginning of the image acquisition, and the software is configured, after determining with the predetermined statistical significance whether at least one hot spot is present in the molecular image, to perform at least one of: (a) providing a recommendation that the image acquisition be stopped before an end of the maximum duration or accumulation of the maximum number of counts of the image acquisition, and (ii) stopping the image acquisition automatically before the end of the maximum duration or accumulation of the maximum number of counts of the image acquisition.

The software algorithm may, for example, characterize the molecular image via image segmentation. In a number of embodiments, the software algorithm includes one or more artificial intelligence algorithms. The software algorithm may, for example, include at least one of a machine learning algorithm, a deep learning algorithm, a pattern recognition algorithm, an image segmentation algorithm, a signal-preserving noise filtering algorithm, or a count-density contouring algorithm.

In a number of embodiments, a time during the image acquisition to initiate a first of the one or more analyses of the molecular image is input and a period of time between consecutive analyses is input.

The system may further include a data communication system to receive data of the molecular image from the molecular imaging system. In a number of embodiments, the molecular imaging system includes a molecular breast imaging (MBI) system, a single photon emission (SPE) planar imaging system, a single photon emission computed tomography (SPECT) system, or a positron emission tomography (PET) system.

In a number of embodiments, the system further includes another software algorithm, wherein, the another software algorithm is configured, after determination with the predetermined statistical significance whether at least one hot spot is present in the molecular image, to measure a characteristic of at least one of (a) a background parenchyma or (b) the at least one hot spot, and to assess a diagnostic significance of the at least one hot spot. The characteristic of the background parenchyma may, for example, be a standardized uptake value of the background parenchyma. The characteristic of the at least one hot spot may, for example, be selected from the group consisting of a standardized uptake value of the at least one hot spot, a size of the at least one hot spot, and a location of the at least one hot spot.

In a further aspect, a product includes a non-transitory computer readable storage medium having instructions stored thereon, that when executed by a processor, perform actions including: performing one or more analyses of a molecular image after beginning acquisition of the molecular image via a molecular imaging system to determine whether at least one hot spot is present in the molecular image; and subsequently performing at least one of: (i) providing a recommendation that the acquisition of the molecular image be stopped, and (ii) stopping the acquisition of the molecular image automatically.

In still a further aspect, a product includes a non-transitory computer readable storage medium having instructions stored thereon, that when executed by a processor, perform actions including: analyzing a molecular image acquired via a molecular imaging system to determine whether at least one hot spot is present in the molecular image, measuring at least one of (i) a characteristic of a background parenchyma of the molecular image and (ii) a characteristic of the at least one hot spot, and assessing a diagnostic significance of the at least one hot spot.

The present devices, systems, and methods, along with the attributes and attendant advantages thereof, will best be appreciated and understood in view of the following detailed description taken in conjunction with the accompanying drawings.

Figure 1A:
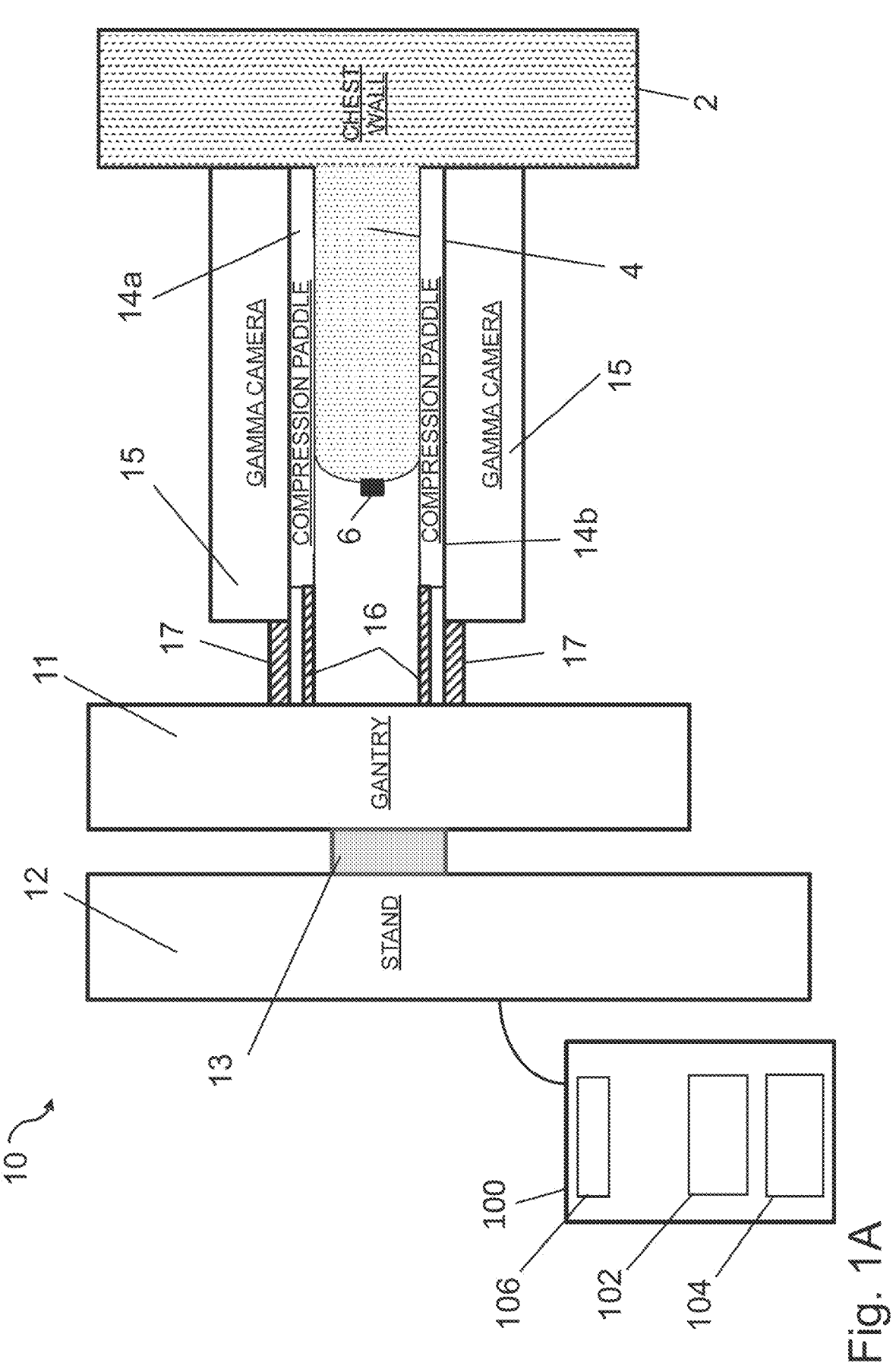
FIG. 1A illustrates a side, schematic view of an embodiment of an MBI system with gantry and electronic circuitry capable of implementing adaptive intelligence in accordance with embodiments hereof.

The present devices, systems, and methods, along with the attributes and attendant advantages thereof, will best be appreciated and understood in view of the following description taken in conjunction with the accompanying drawings.

DESCRIPTION

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "an algorithm" includes a plurality of such algorithms and equivalents thereof known to those skilled in the art, and so forth, and reference to "the algorithm" is a reference to one or more such algorithms and equivalents thereof known to those skilled in the art, and so forth. Recitation of ranges of values herein are merely intended to serve as a shorthand method of referring individually to each separate value falling within the range. Unless otherwise indicated herein, each separate value, as well as intermediate ranges, are incorporated into the specification as if individually recited herein. All methods described herein can be performed in any suitable order unless otherwise indicated herein or otherwise clearly contraindicated by the text.

The terms "electronic circuitry", "circuitry" or "circuit," as used herein include, but are not limited to, hardware, firmware, software, or combinations of each to perform a function(s) or an action(s). For example, based on a desired feature or need, a circuit may include a software controlled microprocessor, discrete logic such as an application specific integrated circuit (ASIC), or other programmed logic device. A circuit may also be fully embodied as software. As used herein, "circuit" is considered synonymous with "logic." The term "logic", as used herein includes, but is not limited to, hardware, firmware, software, or combinations of each to perform a function(s) or an action(s), or to cause a function or action from another component. For example, based on a desired application or need, logic may include a software controlled microprocessor, discrete logic such as an application specific integrated circuit (ASIC), or other programmed logic device. Logic may also be fully embodied as software.

The term "processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

The term "controller," as used herein includes, but is not limited to, any circuit or device that coordinates and controls the operation of one or more input and/or output devices. A controller may, for example, include a device having one or more processors, microprocessors, or central processing units capable of being programmed to perform functions.

The term "software," as used herein includes, but is not limited to, one or more computer readable or executable instructions that cause a computer or other electronic device to perform functions, actions, or behave in a desired manner.

The instructions may be embodied in various forms such as routines, algorithms, modules, or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, or the desires of a designer/programmer or the like.

In a number of embodiments hereof, a molecular image is analyzed repeatedly during the acquisition thereof to determine whether at least one hot spot is present in the image. When it becomes statistically significant that either there is or is not at least one hot spot present in the image a recommendation may be made that the image acquisition be stopped early, or the image acquisition may be automatically stopped early.

In a number of other embodiments, a molecular image is analyzed to determine whether any hot spots (which may, for example, correspond to "lesions" or areas of abnormal tissue) are present. Upon determination of the presence of at least one hot spot, at least one characteristic of a background parenchyma or of the hot spot is measured. The at least one characteristic may, for example, include at least one of a standardized uptake value of the background parenchyma or a standardized uptake value, a size, or a location of the hot spot. After measuring at least one characteristic of the background parenchyma or of the hot spot, a diagnostic significance of the (at least one) hot spot is assessed.

Devices, systems, and methods hereof may, for example, be used in connection with non-invasive molecular imaging such as molecular breast imaging (MBI), single photon emission (SPE) planar imaging, single photon emission computed tomography (SPECT), or positron emission tomography (PET). In general, molecular imaging is a branch of medical imaging that concentrates upon imaging molecules of medical interest within a patient. In a number of embodiments hereof, devices, system and methods use computer-implemented algorithms such as artificial intelligence algorithms in characterizing molecular images to, for example, provide clinical decision support (CDS) and/or adaptive intelligence support to a radiologist to screen for disease, diagnose a disease, monitor therapy, or to guide a surgical intervention. Such surgical interventions may, for example, include biopsy sampling, surgical excision, insertion of radioactive seed (brachytherapy), therapeutic deliver (for example, drug, stem cell, or other therapy delivery), guide wire or marker insertion and ablation device insertion. In a number of embodiments, one or more artificial intelligence algorithms are used in characterizing images in the devices, systems and/or methods hereof. In a number of embodiments, one or more machine learning algorithms (a subset of artificial intelligence) may be used in characterizing images.

Molecular breast imaging or MBI is described herein in a number of representative examples of application of artificial intelligence algorithms or models via the devices, systems, and methods hereof to molecular imaging. However, one skilled in the art appreciates that such applications of devices, systems and methods hereof to MBI are representative examples and that the principles of the devices, systems, and methods hereof are equally applicable to other molecular imaging techniques such as SPE, SPECT, and PET imaging. Moreover, those skilled in the art appreciate that organs/regions of interest other than the breast (such as the prostate, the brain, etc.), or diseases other than cancer (such as epilepsy, multiple sclerosis, etc.), also may benefit from using the devices, systems and/or methods hereof.

Advantages provided by the devices, systems, and methods hereof include, but are not limited to 1) significantly shorter exam times and, thus, increased patient throughput, less patient motion from long-exam fatigue, and reduced exposure to imaging radiation, 2) clinical decision support that facilitates rapid learning by breast radiologists of a new modality such as MBI, 3) clinical decision support that facilitates greater consistency and confidence in analysis of MBI (and/or other) images, and 4) quantitation of standardized uptake values (SUVs) for background tissue and hot spots which enables new clinical risk assessments (for example, for risk for developing breast cancer based upon background tissue SUV), and therapy monitoring.

Figure 1B:
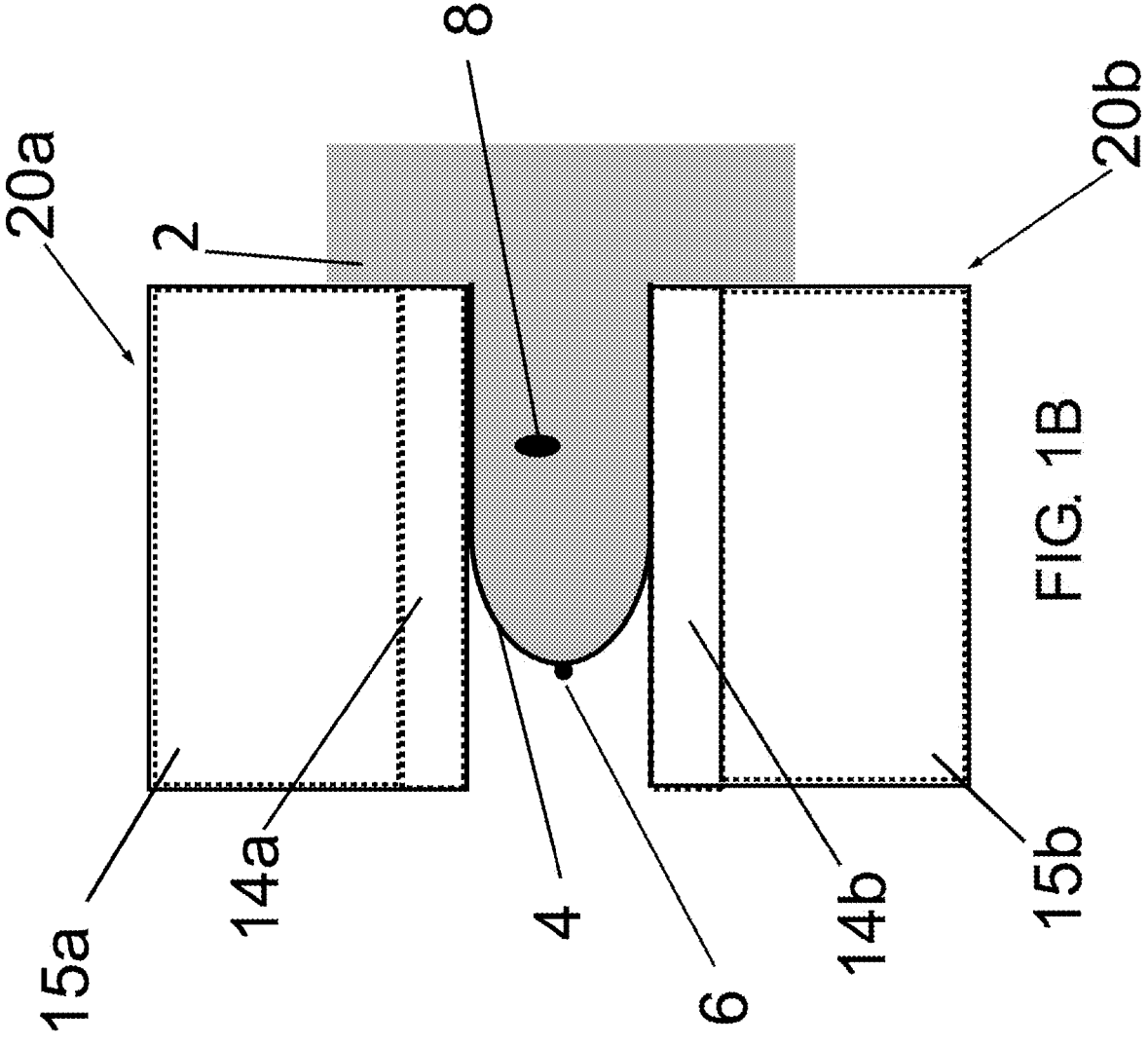
FIG. 1B illustrates an isolated, schematic view of the physical arrangement of a molecular breast imaging device in relation to a breast.

FIG. 1A illustrates an embodiment of an MBI system 10 that can be used in connection with the methodologies hereof. FIG. 1A shows a cross-sectional side view with gantry 11 on the left and the patient's chest wall 2 on the right with breast 4 and nipple 6 positioned toward gantry 11. Thin compression paddles 14 a and 14b (for example, formed from a transparent polymeric or plastic material such as an acrylic or carbon fiber) directly contact and immobilize breast 4. Compression paddles 14 a and 14b are optional for screening or diagnostic MBI but at least one is required for MBI-guided biopsy. An isolated view of compression paddles 14a and 14b and breast 4 is illustrated in FIG. 1B. Two gamma cameras 15 are positioned in contact with compression paddles 14a and 14b. If compression paddles 14a and 14b are not present in the MBI system 10 then the gamma cameras 15 may directly contact breast 4 and provide the mild compression needed to immobilize the breast. Those skilled in the art will appreciate that electronic circuitry 100, including, for example, a processor system 102 in operative connection with a memory system 104, may include software including one or more algorithms stored in memory system 104 and executable by processor system 102 to operate as a control system or controller to independently control motion of the gantry 11, rotor 13, gamma cameras 15, and compression paddles 14a and 14b. Electronic circuitry 100 may also operate to acquire, process, and display the gamma emission images collected during the MBI examination. Alternatively, manual control can be used to adjust the positions of gantry 11, rotor 13, gamma cameras 15, and compression paddles 14a and 14b and to control image acquisition by the cameras 15. Processor system 102 (which may, for example, include one or more processors and/or microprocessors) of electronic circuitry 100 may also execute software stored in memory system 104 including one or more models/algorithms that implement one or more algorithms or sub-algorithms such as algorithms 600 and 800 as described herein. As known in the computer arts, an input/output system 106 may be in operative connection with processor system 102 and memory system 104 to acquire data input from MBI system 10 and/or one or more users and to output data/information. Although software algorithms hereof may be executed via electronic circuitry 100 of system 10, one skilled in the art appreciates that such algorithms may, for example, be stored and executed separately (for example, via a separate computer) or that storage of such algorithms and execution thereof may be distributed over a number of devices or systems.

As known in the art, the gantry assembly may, for example, include gantry 11 which supports compression paddles 14a and 14b and gamma cameras 15. Gantry 11 may, for example, be rotatably connected by a rotor 13 to a stand 12 which supports the weight of the gantry assembly and provides power and data transmission between the gamma cameras 15 and the electronic circuitry 100.

In a number of embodiments, two gamma cameras 15 are used in system 10, but a single camera can be used to reduce system cost at the expense of higher dose or longer exam time. Alternatives with more than two small cameras may also be used.

As known to those skilled in the art of molecular imaging, gamma cameras 15 include a collimator and a detector assembly. In a preferred embodiment, the collimator may have a pixel-registered square parallel-hole core and the detector assembly may be an array of square pixelated CZT detectors. The collimator may, for example, include parallel-hole, slant-hole, focusing (convergent or divergent), multiple-pinhole collimators, or Compton camera (a form of "electronic collimation"). For pixelated detectors, pixel-registered square-hole collimators are preferred, but traditional hexagonal-hole collimators can also be used. Alternatively, the detector assembly 15 may include a scintillator (pixelated or monolithic) and an array of photodetectors, such as vacuum photomultiplier tubes (PMTs), position-sensitive PMTs-PSPMTs, avalanche photodiodes (APDs), or solid-state photomultipliers (also called silicon photomultipliers or SiPMs).

Compression paddles 14a and 14b may be a transparent polymeric, carbon fiber, or other suitable material. Alternatively compression paddles 14a and 14b may be made of thin carbon fiber. There can be multiple varieties of compression paddles (as in mammography) suitable for use herein, of which some are solid, and some include apertures of various sizes for biopsy or surgery access. Compression paddles 14a and 14b need not be planar. They may, for example, be contoured (for example, arced or curved) to better conform to the shape of breast 4. Gamma cameras 15 can also be contoured (for example, arced or curved), especially when composed of modular pixelated detectors, to fit the curvature of compression paddles 14a and 14b.

Compression paddles 14a and 14b and gamma cameras 15 are each mechanically attached by separate support arms (16 and 17, respectively) to the MBI gantry 11. Compression paddles 14a and 14b are typically mechanically independent of the gamma cameras 15. Compression paddle support arms 16 are directly connected to gantry 11. Gamma camera support arms 17 are able to position gamma cameras 15 in direct contact with thin compression paddles 14a and 14b, when present, so that gamma cameras 15 are as close as possible to breast 4, which will optimize the image quality (as will be apparent to those skilled in the art). However, gamma cameras 15 do not directly contact breast 4 and do not provide any compressive force on breast 4 as, for example, described in U.S. Pat. No. 6,377,838. However, compression paddles 14a and 14b are required only for MBI-guided biopsy. If they are absent, then gamma cameras 15 do directly contact the breast and do provide the mild compressive force required to immobilize the breast 4. As will be apparent to those skilled in the art, the configuration of system 10 with compression paddles 14a and 14b places the gamma cameras 15 further away from breast 4, typically by a fraction of a centimeter, thus at a slight disadvantage with respect to U.S. Pat. No. 6,377,838, but with significant advantages in clinical practice. The typical design of a compression paddle 14a and 14b, as is well-known by those skilled in the art, is similar in geometry to a cut-away of the bottom of a box. That is, the paddle includes a bottom surface that contacts breast 4 and there are four perpendicular sides to give mechanical strength to the paddle. Those four sides and bottom constitute a "well" into which gamma camera 15 can be designed to fit loosely. In a number of embodiments, compression paddles 14a and 14b are each connected by at least two support arms 16 to the compression mechanism of the gantry 11. Gamma cameras 15 are each connected by support arms 17 to the compression mechanism of gantry 11.

Gamma camera support arms 17 may be articulated to tilt, rotate, or otherwise move one or both of gamma cameras 15 out of the immediate vicinity of breast 4 when not imaging. The ability to move a gamma camera 15 out of the way, while keeping breast 4 immobilized by compression paddles 14a and 14b provides an advantage during the positioning of breast 4 prior to imaging and also during biopsy or surgery guidance.

FIG. 1B illustrates an isolated view of a physical arrangement of a molecular breast imaging device in relation to a breast. Typically, mammography (MMG: full-field digital mammography [FFDM], film mammography, or digital breast tomosynthesis [DBT]) is recommended to be performed on a yearly basis for women who are 40 years or older. Recently the US Protective Services Task Force has recommended that women receive bi-annual mammograms between the ages of 40 and 74. About half of women have radiographically dense breasts that can obscure the presence of breast cancer, so that mammography only detects about half of cancers in dense breasts. In women with radiographically dense breast parenchyma, additional breast examinations should be performed. The National Comprehensive Cancer Network [NCCN], one of the critical groups providing clinical practice guidelines in oncology, recommends (1) MRI, then (2) Contrast Enhanced Mammography [CEM] or MBI when MRI is not available, and only then (3) DBT or US when MRI, CEM or MBI are not available. MRI, CEM and MBI are the most effective supplemental screening modalities today for detecting cancer in dense breast women, where MBI is about 25% of the cost of MRI.

If the results of the MMG examination are equivocal or require further study before a clinical plan can be determined, then the patient may be referred for molecular breast imaging (MBI) for secondary diagnosis. In other cases, once a mammogram has shown that a woman has dense breast tissue, the referring physician may decide to forego annual screening mammography and send the woman for an annual MBI screening study. In still other cases, one or more hot spots ("lesions") may be found on MBI and the woman may undergo neoadjuvant chemotherapy to treat the hot spots before any potential surgical intervention. MBI may be used to monitor the progress of such therapy. Another application for MBI is to guide surgical intervention, such as biopsy or lumpectomy of the one or more hot spots detected by MBI.

FIG. 1B illustrates breast 4 mildly compressed between an upper detector assembly 20a and a parallel lower detector assembly 20b. Detector assemblies 20a and 20b may, for example, each include an optional compression paddle 14a and 14b, respectively, in addition to the gamma cameras 15, which are illustrated in broken lines in FIG. 1B. The detector assemblies 20a and 20b are mounted on a gantry (as described above) and are typically positioned adjacent to the chest wall 2. In FIG. 1B, a mass-like hot spot 8 is depicted. The illustration of FIG. 1B is intended to represent several common configurations of MBI devices. In one such device, both the upper and lower detector assemblies 20a and 20b include a gamma photon detector and a collimator. There are two types of gamma photon detectors currently deployed by the several companies that offer commercial MBI systems. The older technology utilizes a scintillator (typically NaI or CsI, monolithic or pixelated) with a photodetector (typically avalanche photodiodes [APDs] or photomultiplier tubes [PMTs]). The newer technology utilizes direct-conversion solid-state semiconductor detectors (typically CdZnTe [CZT] or CdTe). The devices, systems and methods hereof apply to single detector MBI systems as well as the more sensitive dual-detector MBI systems and other gamma camera systems as will be obvious to those skilled in the art. In another type of MBI device, both the upper and lower detector assemblies 14a and 14b include gamma photon detectors configured for coincidence event detection as part of a Positron-Emission Mammography (PEM) system, which requires no physical collimator. In that case, the gamma photon detectors utilize a scintillator (typically LYSO or other PET scintillator) and a photodetector (typically APDs or silicon photomultipliers [SiPMs]).

In MBI, a small dose of, for example, Tc99m-Sestamibi (or Tc99m-Tetrofosmin), which is a radiopharmaceutical that is taken up by cells with a high concentration of mitochondria, is injected intravenously (i.v.) into the woman and the molecules of the agent are preferentially and relatively rapidly taken up by the abundant mitochondria in breast cancer cells. The radiologist may make a trade-off between radiation dose and imaging time in choosing how much radiotracer to inject. The Mayo Clinic has demonstrated that 10-minute per view MBI screening exams are feasible at a dose of 4 mCi Tc99m-Sestamibi (currently an off-label use).

In PEM, the tracer is typically fluorodeoxyglucose ($^{18}$F) or FDG (a radiopharmaceutical which is a marker for tissue uptake of glucose). The patient is typically positioned in a chair with one breast lightly compressed (about ⅓ the force needed for x-ray mammography) to immobilize the breast between two parallel-opposed small gamma cameras. The patient may also be positioned in lateral decubitus, which is lying on her side on a bed or table. MBI imaging typically begins within 5 minutes or less after i.v. injection of Tc99m tracer. However, in PEM the patient may rest for an hour or more before imaging to allow washout from background tissue. In common clinical practice, the two breasts are generally imaged one at a time and in two orientations each: generally parallel to a body-axis line of view called the craniocaudal or CC view, and along an approximately 40-60 degrees offset line of view imaging the breast and axilla called the medio-lateral oblique or MLO view. In some circumstances, an approximately 90 degree offset line of view called the lateral view will be substituted for the MLO view. There is no technical requirement to image the two breasts separately or in only two standard MMG views.

After performing an MBI screening or secondary diagnostic examination, a qualified breast radiologist will interpret the molecular images and determine whether a biopsy of any suspicious hot spot should be performed to determine if the hot spot is malignant. If the radiologist determines that a biopsy is required, then an MBI-guided biopsy or a second-look ultrasound may be performed to guide biopsy needle sampling of the suspicious hot spot if it is visible. MBI studies at the Mayo Clinic demonstrate that about 85% of hot spots detected by MBI can also be visualized by ultrasound. An ultrasound-guided biopsy is quick and reimbursable. The ultrasound-guided biopsy may be performed while the breast is still mildly compressed in the MBI system. The advantage is that the biopsy cavity and extracted tissue samples may be imaged by MBI immediately following the biopsy.

In the 15% of cases where an MBI detected hot spot is occult on ultrasound, an MBI-guided biopsy should be performed, although it is possible to substitute an MRI-guided biopsy. MRI-guided biopsy is a lengthy and expensive procedure, often uncomfortable and distressing to the patient who must remain prone with arms raised above her head for a long time (up to two hours). Thus, an MBI-guided biopsy may be preferable.

After a woman is informed that she has radiographically dense breasts, she may benefit more by a regular MBI screening exam. It should be noted that the FDA has cleared MBI for diagnostic imaging and supplemental breast cancer screening is off label.

Figure 2:
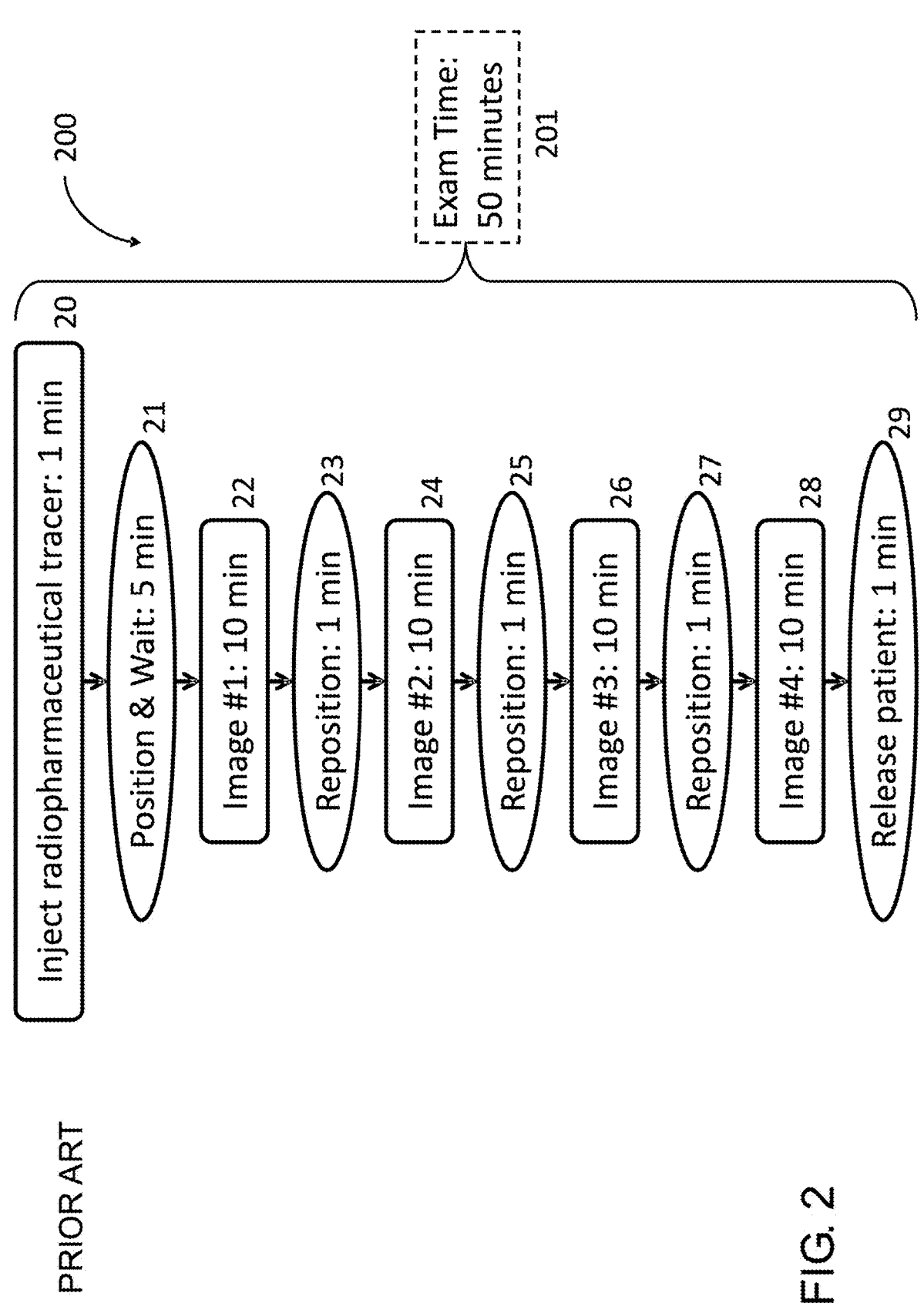
FIG. 2 illustrates a typical clinical workflow for MBI as currently practiced.

FIG. 2 illustrates a representative example of a currently typical clinical workflow 200 for MBI including various procedures, actions, or steps. A typical exam time 201 is currently 50 minutes for four views, consisting of two views per breast. Thus, only one patient per hour can be scheduled and the patient is likely to grow tired of the imaging and be susceptible to movement that can compromise image quality. The patient will typically remove her shirt/top and bra, then don a patient gown open at the front. A breast technician or nurse will insert an i.v. port, usually in an arm. These preparation steps are not included in FIG. 2. Upon entering the MBI exam room (or just before entering), the technician will inject the radiopharmaceutical tracer into the patient's i.v. port (step 20). During the next 5 minutes or less, the breast technologist will seat the patient in the examination chair and position one breast in the MBI system, typically in the CC orientation, and will immobilize the breast with mild compression (step 21). Step 22 includes acquiring for 10 minutes image #1 of the first breast. In step 23, the first breast is repositioned and immobilized, typically in the MLO orientation. Step 24 includes acquiring for 10 minutes image #2 of the first breast. In step 25 the technician positions and immobilizes the other breast in the MBI system, typically in the CC orientation. Step 26 includes acquiring for 10 minutes image #3 of the second breast. In step 27, the second breast is repositioned and immobilized, typically in the MLO orientation. Step 28 includes acquiring for 10 minutes image #4 of the second breast. After 4 images are acquired, the patient is released from the exam room and permitted to dress in her clothes (step 29). The order of imaging is flexible and can be varied.

Figure 3:
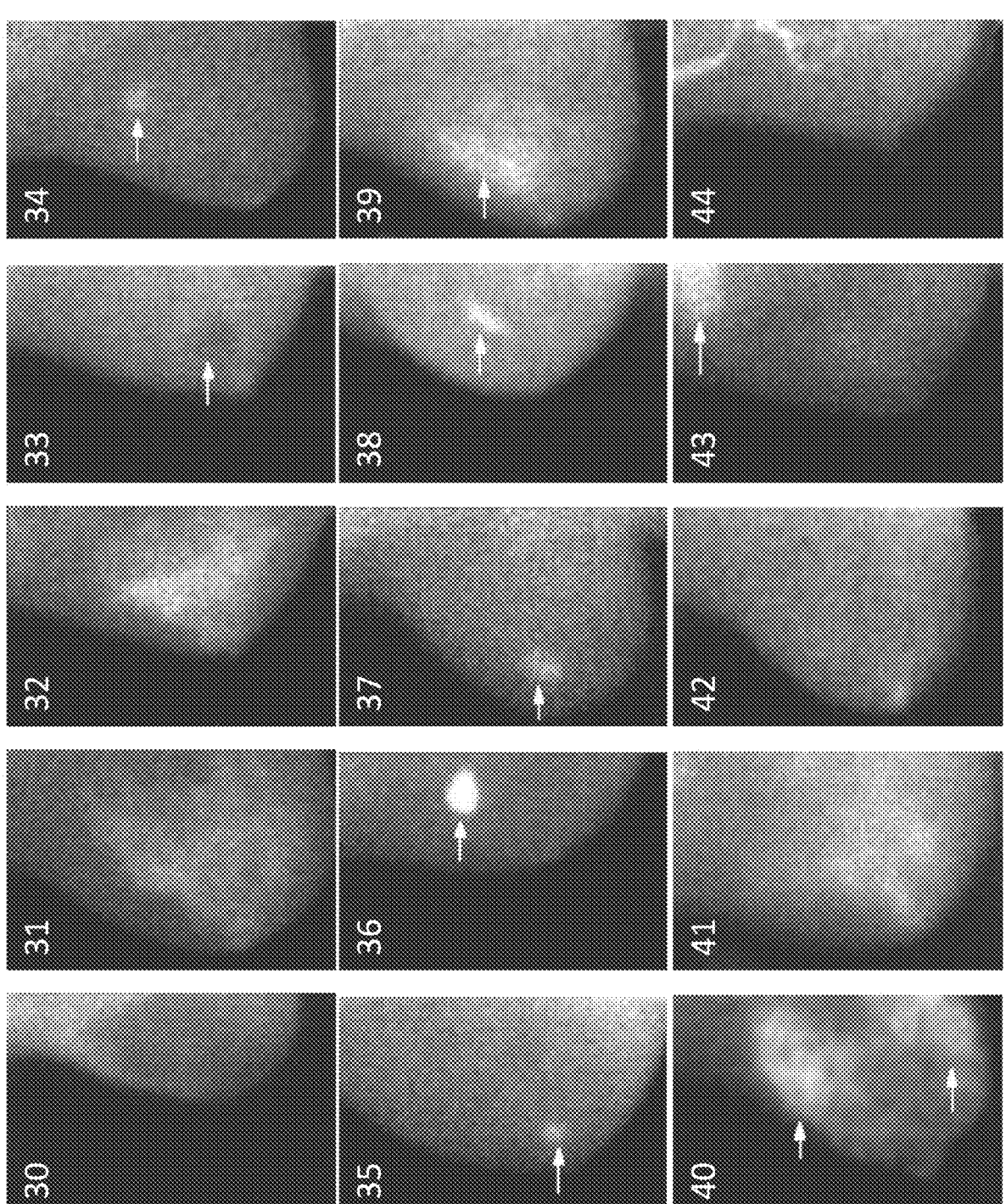
FIG. 3 illustrates typical molecular breast images that exhibit focal or diffuse regions of significantly increased tracer uptake with respect to background.

FIG. 3 illustrates typical molecular breast images 30-44 that exhibit focal or diffuse regions of significantly increased (or occasionally decreased) tracer uptake (hot spots or "lesions") with respect to background parenchyma (the remainder of the breast tissue image other than any identified hot spots). In some images a white arrow has been overlaid to identify the suspicious hot spot. Each of these images provided by courtesy of the Mayo Clinic was acquired with an injection of 6-8 mCi of Tc99m-Sestamibi and each image was acquired for 10 minutes.

Figure 4:
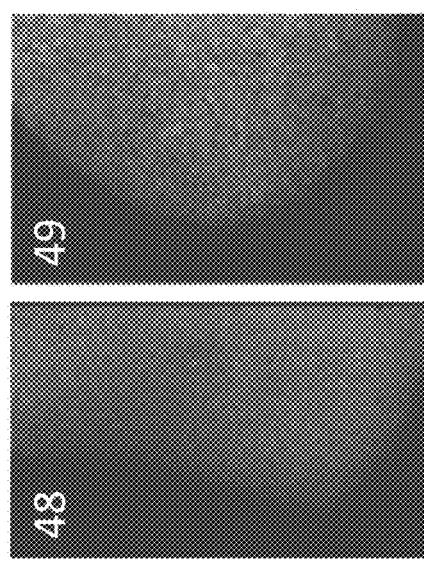
FIG. 4 illustrates typical molecular breast images that exhibit uniform tracer uptake.

FIG. 4 illustrates typical molecular breast images 48 and 49 that exhibit uniform background parenchyma tracer uptake without any significant hot spots, such as those in FIG. 3. Each of these images provided by courtesy of the Mayo Clinic was acquired with an injection of 6-8 mCi of Tc99m-Sestamibi and each image was acquired for 10 minutes.

Figure 5:
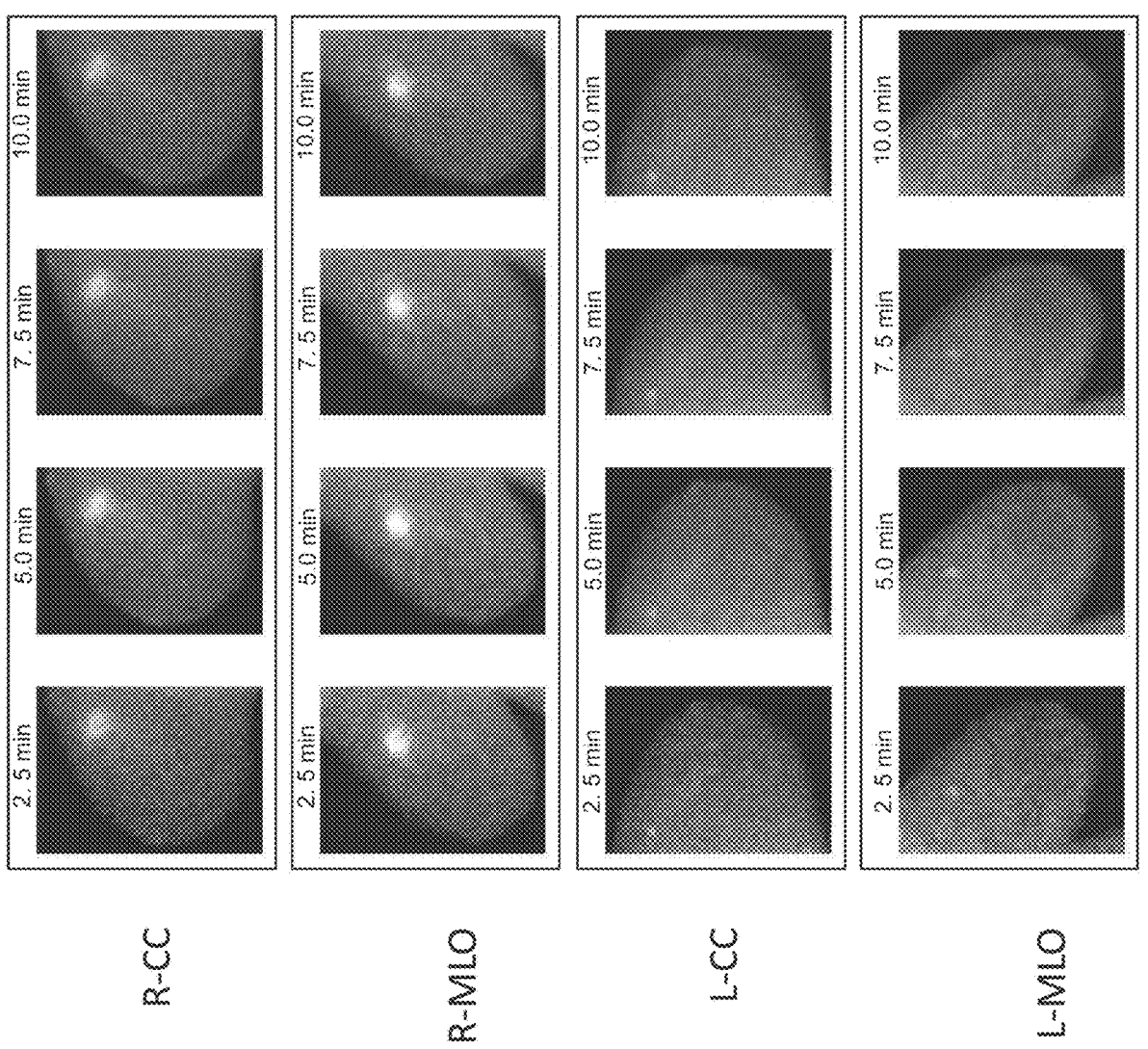
FIG. 5 illustrates the time evolution of molecular breast images in cases of focal regions of significantly increased tracer uptake with respect to background.

FIG. 5 illustrates the time evolution of molecular breast images in cases of focal regions of significantly increased tracer uptake with respect to background parenchyma. Two breasts are shown: the top two rows of images show a right breast with a large focal hot spot and the bottom two rows show a left breast with a small focal hot spot. Each breast is shown in the two common views, CC and MLO. In addition, 4 time points are shown for each breast and orientation: the 1sts column shows 2.5 minutes of acquisition, $2^{nd}$ column 5.0 minutes, $3^{rd}$ column 7.5 minutes, and $4^{th}$ column 10 minutes. Each of these images provided by courtesy of the Mayo Clinic was acquired with an injection of 6-8 mCi of Tc99m-Sestamibi. The images of FIG. 5 demonstrate that the shortest acquisition time, 2.5 minutes in this example, is more than adequate to identify the hot spot and draw the conclusion that a biopsy should be performed. The acquisitions could have been shortened by at least a factor of 4 if there had been a protocol in place to facilitate stopping the acquisition earlier than 10 minutes. This observation has been repeated in many patients over multiple clinical sites.

Figure 6:
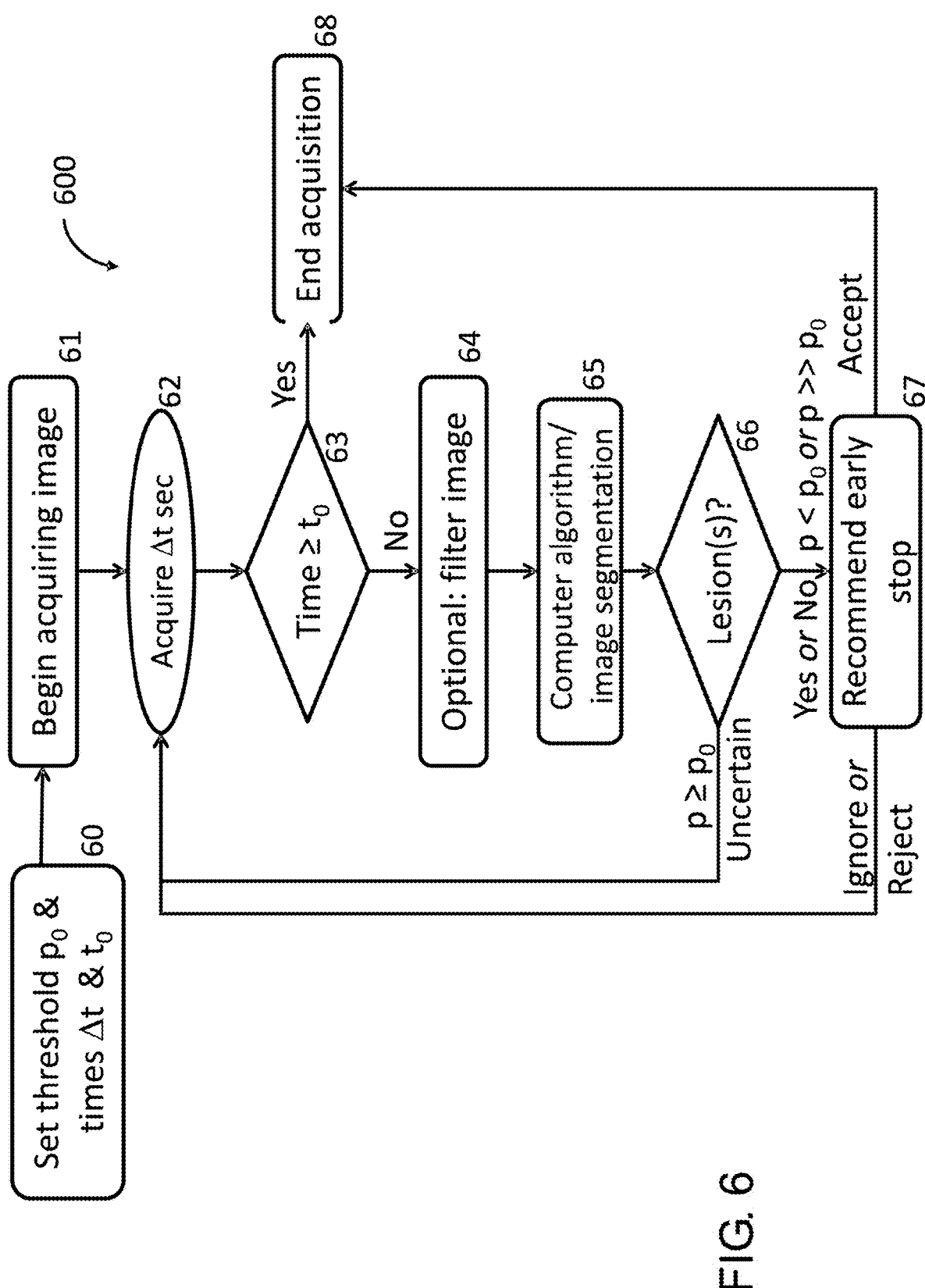
FIG. 6 illustrates an algorithm or artificial/adaptive intelligence algorithm for clinical decision support for determining when sufficient events have been acquired in accordance with embodiments hereof.

FIG. 6 illustrates an algorithm or methodology 600 including use of one or more algorithms or models (for example, computer aided detection algorithms and/or other algorithms), which may include artificial intelligence (such as machine learning and/or deep learning algorithms or models) for analyzing an image during acquisition thereof. Upon a determination that a sufficient threshold or significance/confidence level has been reached in characterizing the image (for example, that one or more hot spot are present), a recommendation to the MBI technician that the image acquisition be stopped can be made in providing clinical decision support. Alternatively, the image acquisition may be stopped automatically (that is, via electronic circuitry controlling/characterizing the imaging procedure). The embodiment of FIG. 6 is illustrative only. Algorithms other that those specifically illustrated in FIG. 6 may be used in the methodologies hereof. In a number of embodiments, a goal of the illustrative algorithm is to monitor a molecular image acquisition (for example, MBI, PET, SPECT) and to test the hypothesis $H_1$, after each partial image acquisition 62 of duration $\Delta t$, that there is a hot spot in the field of view versus the null hypothesis. When sufficient data have accumulated to test the hypothesis $H_1$ at a preset significance level $p_0$ (type I error, false positive), then the algorithm may recommend to the MBI technician that the image acquisition can be stopped because there is no benefit to collecting more data. Step 60 sets the variable parameters for the algorithm. Typically, $p_0$ is chosen as 5% for clinical tests. At is the incremental time between each repeated image analysis (for MBI, one may typically choose between about 10 and 30 seconds). The $\Delta t$ parameter may, for example, be optimized for computer processing speed. The $\Delta t$ parameter and/or other parameters may also vary during the image acquisition in a predetermined manner. For example, $\Delta t$ may be reduced as the acquisition proceeds or as a threshold in statistical significance is approached. The parameter to is the default image acquisition time duration. For MBI, to is typically set between 5 and 10 minutes, depending on patient dose of tracer. One skilled in the art will recognize that an alternative method for automatically ending an image acquisition is to set a maximum number of counts for the image. Whether a default duration or a default count limit is used, the present devices, systems, and methods may be used to provide a recommendation that the image acquisition be stopped before an end of the maximum duration/count of the image acquisition and/or to automatically end the image acquisition. More than one threshold or significance/confidence levels may be predetermined and associated with taking various different actions.

Step 61 marks the start of an image acquisition, where the accumulated time is set to 0 and step 62 is a state of waiting for an interval $\Delta t$ while the gamma cameras 15 count gamma emission events. At step 63, the accumulated time is compared to the default acquisition duration to. If the accumulated time equals or exceeds to, then step 68 (end acquisition) is reached. If the accumulated time is still less than to, then the image analysis commences with optional step 64 (filter image). This image filter may comprise, for example, a signal-preserving denoising filter such as BM3D (Block Matching and 3D filtering), principal component analysis (PCA), wavelet denoising, or other methods known to those skilled in the art. This image filtering could also comprise an image reconstruction technique to combine the images of the two opposed detector arrays as well as applying a model of the collimator-detector response to provide "resolution recovery." Step 64 is optional, but often useful to enhance the computer analysis/characterization of the most recently acquired image initiated in Step 65. As known in the computer and artificial intelligence arts, the image may be segmented. Image segmentation may, for example, include dividing an image input into segments (or regions or clusters) to simplify image analysis (for example, sets of pixels). Segmentation algorithms and tumor identification are, for example, discussed in Singh, S., et al., "Current Methods in Medical Image Segmentation, A Review," International Conference on Communications, Computing and Systems, p. 199 (2014); Pham, D. L. et al., "Current Methods in Medical Image Segmentation," *Annual Review of Biomedical Engineering*, (2000) 2:315-337; A Hosny, C Parmar, J Quackenbush, et al. "Artificial intelligence in radiology", *Nature Reviews Cancer*, (2018) 18:500-510, the disclosures of which are incorporated herein by reference. In a number of embodiments, the algorithm or model determines if there is evidence in the image of at least two clusters: one cluster representing one or more hot spots and a second cluster representing the background parenchyma. The background does not have to be completely uniform. For example, in MBI there may be an increase in count density near the chest wall as a result of scattering of primary gamma photons emitted from the heart, then Compton scattered by breast tissue, ribs, or chest muscle into the detector. In step 65, an image segmentation algorithm may take this normal spatial variation of the background tissue into account.

Hot spots may have different appearance, such as those depicted in FIG. 3 and FIG. 5. Tumors are usually brighter (higher count density) than the background tissue by a factor of 5 to 25, depending on hot spot type and size. However, there can be "cold" spots, such as the cyst depicted in image 33 in FIG. 3. This image segmentation (cluster analysis and classification) step may be performed by, for example, machine learning (data mining) or pattern recognition analysis (histograms and spatially connected regions) or by count-density contouring (level-set methods). An illustrative detailed algorithm will be discussed below in connection with FIG. 8.

An alternative embodiment of step 65 comprises manual identification of a hot spot by the MBI technician. For example, as the image is being acquired, the technician could identify (for example, point to and click or encircle) one or more apparent hot or cold spots. The software algorithm could, in real time as the acquisition continues, draw a contour around each identified spot. The statistical hypothesis testing could then be performed as the image acquisition continues.

In the embodiment of FIG. 6, the output of image segmentation step 65 is a statistical p-value for the hypothesis H: that there is a hot spot in the field of view. If $p \geq p_0$ by a modest amount and p is trending toward $p_0$, then the hot-spot-present hypothesis is still uncertain and additional data should be acquired to increase the hot-spot-to-background contrast ratio. In this case, step 62 is repeated.

Step 66 tests the hypothesis $H_1$ that one or more hot spots are present. If p is much greater than $p_0$ and is not trending toward $p_0$, the null hypothesis He may be assumed true. If $p < p_0$, then the hot-spot-present hypothesis $H_1$ is apparently true. In either of these two cases, sufficient data have been acquired to detect a hot spot. The next step is 67 (recommend early stop). This is the adaptive intelligence consequence of this algorithm: the count density required to determine whether a hot spot is present is data dependent and varies from patient to patient. Following a recommendation to stop acquisition, the image acquisition continues while this recommendation is pending a response from the technician. In a number of embodiments, the technician must choose whether to accept or reject or ignore the software recommendation to stop the acquisition. Each breast radiologist could specify a different response to the software recommendation for an early stop to the image acquisition. For example, one radiologist might instruct the technician to always accept the software recommendation. Another might instruct the technician to acquire an additional 2 minutes after the software recommendation to stop. Another might want to see the images in real time at a remote workstation or on a tablet computer so that they, rather than the technician, can decide when to stop the image acquisition. As breast radiologists gain experience with the software recommendations, they may, for example, more readily accept the software recommendations and thus, greatly reduce the average examination time, enabling a larger throughput of patients, as illustrated in the next figure.

Figure 7:
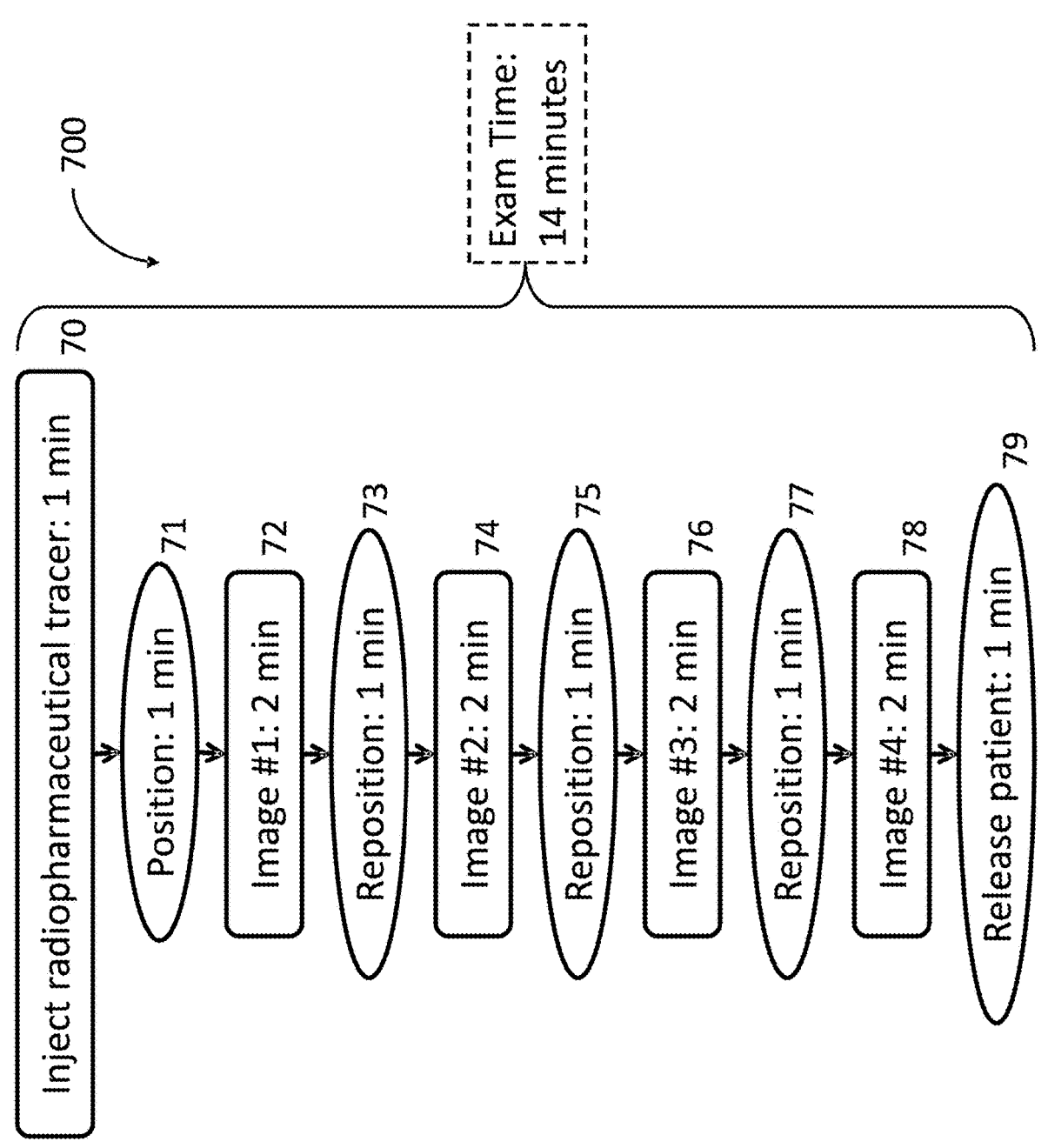
FIG. 7 illustrates a typical clinical workflow for MBI in the case where early acquisition stop decisions have been made in accordance with embodiments of devices, systems, and methods hereof.

FIG. 7 illustrates a typical clinical workflow for MBI 700 in the case where early acquisition stop-decisions have been made. It should be compared to FIG. 2 which illustrates a typical clinical workflow where each image acquisition is set to 10 minutes, regardless of the patient. The main difference in FIG. 7 is that each image acquisition is stopped after 2 minutes, which is consistent with the excellent hot-spot-to-background contrast shown in FIG. 5 where 2.5 minutes was more than adequate to identify a hot spot that should be investigated by biopsy. The other difference is that the 5-minute step 21 position and wait has been reduced to the 1-minute position step 71. This follows from clinical experience at Mayo Clinic and others that there is no advantage to waiting 5 minutes for the Sestamibi tracer to be taken up by tumors: the uptake is rapid and requires less than one minute after the i.v. bolus injection. The effect of the 2-minute image acquisitions and elimination of the wait period is a total exam time of 14 minutes, compared to 50 minutes in FIG. 5. Thus, 3-4 patients could be scheduled every hour, rather than the 1 patient per hour that can be accommodated by the current typical clinical workflow of FIG. 5.

Figure 8:
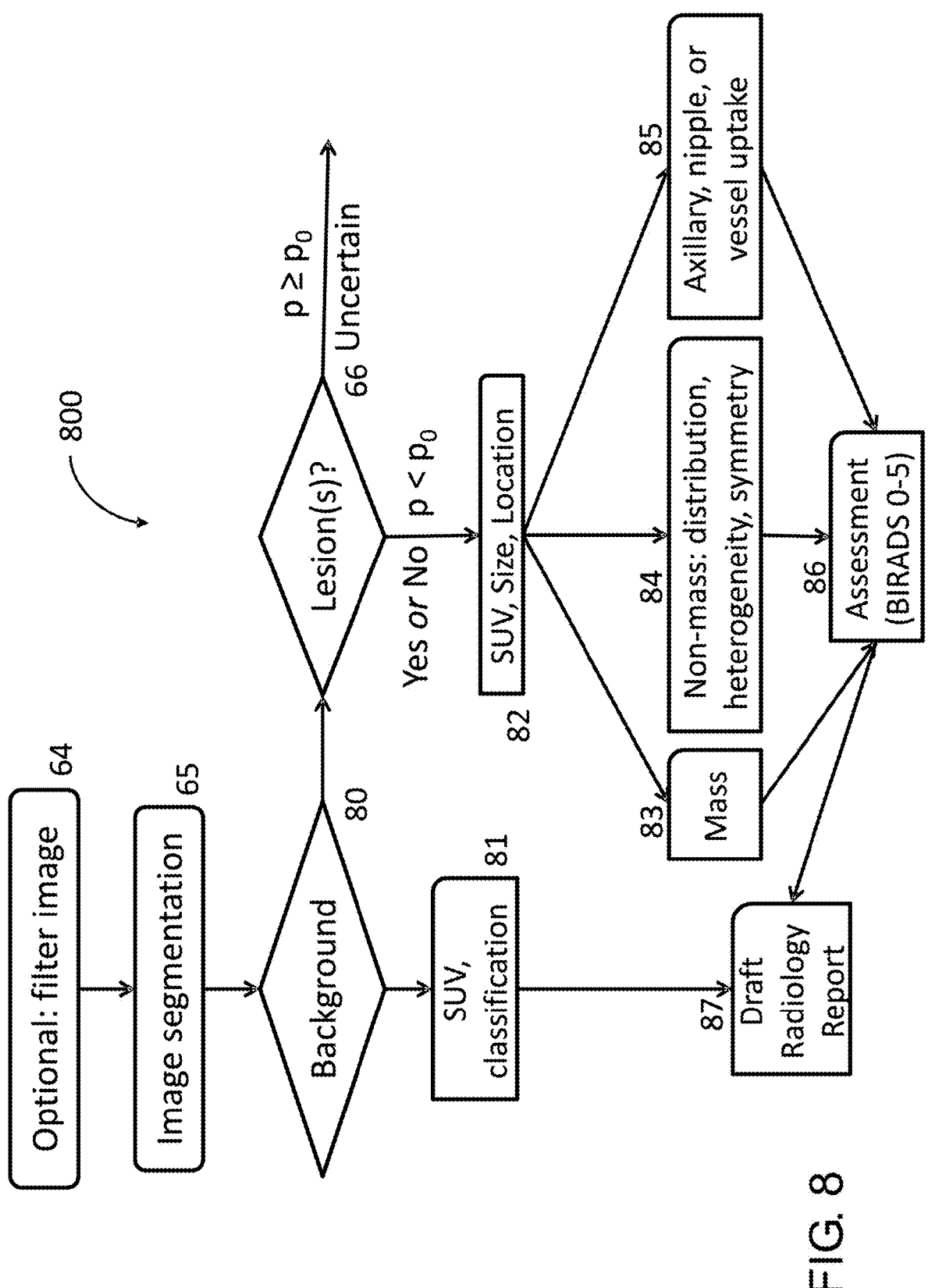
FIG. 8 illustrates an algorithm for clinical decision support that compares an image to a published lexicon for MBI describing the background parenchyma and one or more hot spots (foci of increased activity above background ("lesions"), as in FIGS. 3, 4, and 5) in accordance with embodiments hereof.

FIG. 8 illustrates an algorithm for clinical decision support 800 that, for example, compares an image to a published lexicon for MBI (see Table 1 below). The algorithm describes the background parenchyma and one or more hot spots (as in FIGS. 3, 4, and 5). Steps 64 (optional image filter), 65 (image segmentation) and 66 (are hot spots/ "lesions" detected?) were included in FIG. 6 and previously discussed. The algorithm in FIG. 8 is typically performed after each image acquisition has been completed (i.e., after steps 72, 74, 76, or 78 in FIG. 7), but it could be performed repeatedly as part of the iterative loop 62-66 in FIG. 6. The performance of the segmentation and classification algorithm 800 will be best when the hot spot to background contrast is strongest, (that is, when the acquisition has completed).

The hot spot identification and clinical decision steps in this algorithm are currently performed manually by breast radiologists when examining MBI images and comparing them to, for example, a published or accepted MBI lexicon (for example, the criteria in Table 1 below). An experienced breast radiologist who has interpreted several hundred MBI studies may not benefit significantly from a computerized clinical decision support to classify background parenchyma and any hot spots. However, MBI can be more useful when quantitation is performed automatically by the AI computer software. See, for example, Mckinney, S M et al. "International evaluation of an AI system for breast cancer screening". *Nature*, (2020) 577:89-94; Kobie, N. "DeepMind's new AI can spot breast cancer just as well as your doctor". *Wired UK*, (1 Jan. 2020); Varghese, J et al. "Effects of computerized decision support system implementations on patient outcomes in inpatient care: a systematic review". *Journal of the American Medical Informatics Association*, (2018) 25:593-602; Moja, L. et al. "Effectiveness of computerized decision support systems linked to electronic health records: a systematic review and meta-analysis". *American Journal of Public Health*, (2014) 104:e12-22, the disclosures of which are incorporated herein by reference.

Also, there is a learning curve for new MBI users. Providing machine learning support can help those less experienced with MBI (and/or other imaging modalities) to produce consistent observations and interpretation of imaging studies.

After any hot spots have been segmented out of the MBI image (step 65), the background parenchyma intensity 80 can be measured and classified according to the lexicon. A computer analysis can determine automatically average SUV (standardized uptake values) to quantitate the classification 81 of the background breast tissue. In future studies, such a quantitation may become an important feature. Researchers at Mayo Clinic hypothesize, but have not yet proven, that women with moderate or marked background tissue uptake of the Sestamibi tracer have a higher risk of developing future breast cancer hot spots than women with photopenic or minimal-mild background uptake.

If hot spots have been identified 66 by the image segmentation 65, then characteristics such as the SUV, size, and location of each hot spot are determined and reported 82 by the AI software algorithm(s) hereof. Then, by automated comparison (for example, via machine learning) to a database of MBI images of both normal and breast cancer patients, the hot spots can be classified as mass (83), non-mass (84; distribution, heterogeneity, and symmetry), and associated findings (85, axillary, nipple, or vessel uptake). Finally, the software algorithm hereof can suggest an assessment 86 of each hot spot as benign, suspicious, or malignant according to the BIRADS assessment scale. A follow-up course of action may also be recommended. The software algorithm hereof can produce a draft radiology report 87 for the MBI exam. Of course, a qualified breast radiologist should read and edit such a report before signing approval.

TABLE 1‡

Indication: Describe clinical problems (if any), history of biopsies (date and results), risk factors, indicate if patient is pre- (last menstrual period [LMP] less than one month ago), peri- (LMP more than one month ago and less than 12 months ago), or postmenopausal (LMP at least 1 year ago), phase of menstrual cycle (if relevant), and TABLE 1‡-continued any use of selective estrogen receptor modulators or medications with estrogenic or progestogenic activity Comparison: Prior breast imaging, including prior gamma camera breast imaging studies (if any) should be reviewed, with the dates and types of prior studies reported Technical Factors: Report dose (MBq) and type of tracer injected and duration of circulation phase (time from injection to imaging). If additional views beyond routine CC and MLO projections were obtained, these should be detailed Limitations: Describe any suboptimal positioning, motion, pixel dropout, "hot pixels", electronic, or other artifacts which are felt to affect image interpretation

| Background | Describe degree of radiotracer uptake in background normal parenchyma, which may be uniform (homogeneous) or patchy (heterogeneous) | |
| --- | --- | --- |
| | Photopenic | Less than subcutaneous fat |
| | Minimal-Mild | Equal to or slightly greater than subcutaneous fat |
| | Moderate | Visually greater than mild, but less than twice as intense as subcutaneous fat |
| | Marked | Visually at least twice as intense as subcutaneous fat |

| Findings: Categories and Terms | | Description |
| --- | --- | --- |
| Mass | | Uptake which has convex outward borders, no interspersed normal uptake, and is seen on two projections (if location is amenable) |
| Non-Mass Uptake | | Uptake distinct from the surrounding tissue that does not fit criteria for a mass, and which usually contains interspersed areas of normal glandular tissue |
| | Distribution | |
| | Focal Area | <25% of a quadrant or <2 cm in diameter in a confined area |
| | Segmental | Uptake in linear or triangular region or cone with apex pointing toward nipple that suggests (but is not specific for) intraductal pathology |
| | Regional | Uptake in a large volume of tissue, ≤2 cm in diameter, not conforming to a ductal distribution; may be geographic |
| | Multiple Regions | Uptake in at least two large volumes of tissue; more than one area of geographic uptake |
| | Diffuse | Uptake distributed throughout the breast |
| Internal pattern of uptake | Homogeneous | Confluent, uniform uptake |
| | Heterogeneous/ Patchy | Variable, nonuniform uptake |
| Symmetry | Symmetric | Similar uptake pattern in both breasts |
| | Asymmetric | More uptake in one breast compared to the other |
| Associated Findings | Axillary uptake | Uptake in the axilla, usually thought to be a lymph node which may or may not be pathologic |
| | Nipple uptake | Radiotracer uptake within the nipple, a physiologic finding if not associated with other suspicious uptake |

TABLE 1‡-continued

| | | | |
|---|---|---|---|
| | | Vessel uptake | Serpiginous linear uptake corresponding with a vessel |
| Location | Breast | Right, left, or bilateral | |
| | In-breast location | Quadrant or clockface location, or specifically in the subareolar or central breast or axillary tail | |
| | Depth/distance from the nipple | Anterior, central, or posterior third or measured distance from the nipple | Measurement is made from the center of the finding and recorded in centimeters |
| Qualitative intensity of uptake in lesion (hot spot) | Photopenic | Uptake in lesion is less than subcutaneous fat (or surrounding background parenchyma)* | |
| | Mild | Uptake which appears to be less than 50% of subcutaneous fat (or background)* | |
| | Moderate | Uptake which appears to be at least 50% of subcutaneous fat (or background)* but not twice as intense as subcutaneous fat (or background)* | |
| | Marked | Uptake which appears to be at least twice subcutaneous fat (or background)* uptake | |
| Lesion (Hot Spot) Size | X | Longest measurement of the lesion, made on whichever image best depicts the lesion | |
| | Y | Measurement orthogonal to X, made using the same image used to define X | |
| | Z | If the lesion is visible on both projections, Z should be an orthogonal measurement made on the projection (CC or MLO) not used to define X/Y | |

| BIRADS Assessment Categories | | | |
|---|---|---|---|
| Incomplete Assessment | 0—Incomplete | Additional imaging is needed before a final assessment can be rendered | |
| Final Assessment | 1—Negative | No lesion found (routine follow-up) | |
| | 2—Benign | No malignant features; e.g., photopenia (routine follow-up) | |
| | 3—Probably benign | Very low probability of cancer (follow-up MBI examination is recommended in 6 months if targeted diagnostic mammogram and ultrasound are negative) | |
| | 4—Suspicious | Intermediate probability of cancer (biopsy is recommended) | |
| | 4a—Low suspicion | Used for a finding which requires intervention but is of low suspicion for malignancy | |
| | 4b—Intermediate suspicion | Used for a finding which is judged to be of intermediate suspicion for malignancy | |
| | 4c—Moderate suspicion (but not classic) | Used for a finding which is judged to be of moderate suspicion for malignancy | |
| | 5—Highly suggestive of malignancy | High probability of malignancy (biopsy is recommended) | |
| | 6—Known biopsy-proven malignancy | Appropriate action should be taken | |

‡from Conners, A. L., et al, "Lexicon for standardized interpretation of gamma camera molecular breast imaging," *Eur J Nucl Med Mol Imaging*, 39: 971-982 (2012).
*The authors of Conners, et al. recommend reference to uptake intensity of subcutaneous fat, rather than background parenchyma, for greater consistency.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method for limiting the duration of molecular image acquisition, comprising:

beginning acquisition of the molecular image via a detector system of a molecular imaging system;

transmitting data of the molecular image from the detector system to electronic circuitry in communicative connection with the molecular imaging system during acquisition of the molecular image, the electronic circuitry comprising a processor system, and a memory system in communicative connection with the processor system, the memory system comprising one or more software algorithms saved therein and executable by the processor system, executing at least one of the one or more software algorithms via the processor system to perform one or more analyses of the molecular image over time during the acquisition of the molecular image to determine in each of the one or more analyses whether at least one area indicative of a lesion is present or absent in the molecular image; and after determining that at least one area indicative of a lesion is present or absent in the molecular image in at least one of the one or more analyses of the molecular image, the electronic circuitry performing at least one of:

(i) causing transmission to a user of the molecular imaging system of recommendation that the molecular image acquisition be stopped before a scheduled end of the molecular image acquisition, and (ii) causing transmission of a signal to the molecular imaging system to stop the molecular image acquisition automatically before a scheduled end of the molecular image acquisition.

2. The method of claim 1 wherein a maximum duration or a maximum number of counts of the image acquisition is set at or before the beginning of the molecular image acquisition and entered into the electronic circuitry, and the method comprises, after determining that at least one area indicative of a lesion is present or absent in the molecular image in at least one of the one or more analyses, performing at least one of:

(i) causing transmission to a user of the molecular imaging system of a recommendation that the molecular image acquisition be stopped before an end of the maximum duration or accumulation of the maximum number of counts of the molecular image acquisition, and (ii) causing transmission of a signal to the molecular imaging system to stop the molecular image acquisition automatically before the end of the maximum duration or accumulation of the maximum number of counts of the molecular image acquisition.

3. The method of claim 2 wherein the at least one of the one or more software algorithms executed by the processor system to determine whether the at least one area indicative of a lesion is present or absent comprises an artificial intelligence algorithm.

4. The method of claim 1 wherein the at least one of the one or more software algorithms executed by the processor system to determine whether the at least one area indicative of a lesion is present or absent comprises an artificial intelligence algorithm.

5. The method of claim 1 wherein the at least one of the one or more software algorithms executed by the processor system to determine whether the at least one area indicative of a lesion is present or absent comprises at least one of a machine learning algorithm, a deep learning algorithm, a pattern recognition algorithm, an image segmentation algorithm, a signal-preserving noise filtering algorithm, or a count-density contouring algorithm.

6. The method of claim 1 further comprising selecting a time during the molecular image acquisition to initiate a first of the one or more analyses of the molecular image and one or more periods of time between consecutive analyses.

7. The method of claim 1 wherein the molecular image is created via molecular breast imaging (MBI), single photon emission (SPE) planar imaging, single photon emission computed tomography (SPECT), or positron emission tomography (PET).

8. The method of claim 1 further comprising, after determining that at least one area indicative of a lesion is present in the molecular image, executing at least one of the one or more software algorithms to measure a characteristic of at least one of (a) a background parenchyma and (b) the at least one area indicative of a lesion, and to assess, via comparison to an established lexicon, a diagnostic significance of the at least one area indicative of a lesion.

9. The method of claim 8 wherein the characteristic of the background parenchyma which is measured is a standardized uptake value of the background parenchyma, and wherein the characteristic of the at least one area indicative of a lesion which is measured is selected from the group of a standardized uptake value of the at least one area indicative of a lesion, a size of the at least one area indicative of a lesion, and a location of the at least one area indicative of a lesion.

10. A method for clinical decision support, comprising:
transmitting data of a molecular image acquired via a molecular imaging system into electronic circuitry, the electronic circuitry comprising a processor system and a memory system in communicative connection with the processor system, the memory system comprising one or more software algorithms saved therein and executable by the processor system, the electronic circuitry being configured to be placed in communicative connection with a database including data for an established lexicon;
executing at least one of the one or more software algorithms via the processor system to analyze the data of the molecular image to determine whether at least one area indicative of a lesion is present or absent in the molecular image; and
if it is determined that at least one area indicative of a lesion is present, executing at least one of the one or more software algorithms via the processor system to measure a characteristic of at least one of (i) a background parenchyma of the molecular image and (ii) the at least one area indicative of a lesion, and to assess, via comparison to the established lexicon upon communication with the database storing data of the established lexicon, a diagnostic significance of the at least one area indicative of a lesion based upon the characteristic which is measured; and
transmitting the diagnostic significance to a clinical user.

11. The method of claim 10 wherein the characteristic of the background parenchyma which is measured is a standardized uptake value of the background parenchyma, and wherein the characteristic of the at least one area indicative of a lesion which is measured is selected from the group consisting of a standardized uptake value of the at least one area indicative of a lesion, a size of the at least one area indicative of a lesion, or a location of the at least one area indicative of a lesion.

12. The method of claim 1 wherein the at least one area indicative of a lesion is a hot spot, a cold spot, or an area indicative of a diffuse lesion.

13. A system, comprising:
a molecular imaging system comprising a detector system, and
electronic circuitry in communicative connection with the molecular imaging system, the electronic circuitry comprising a memory system in which one or more software algorithms are stored, and a processor system in operative connection with the memory system to execute the one or more software algorithms, upon transmission of data of a molecular image from the detector system of the molecular imaging system to the electronic circuitry during acquisition of the molecular image, to (i) perform one or more analyses of the molecular image over time during acquisition of the molecular image, (ii) determine in each of the one or more analyses whether at least one area indicative of a lesion is present or absent in the molecular image, and (iii) after determining that at least one area indicative of a lesion is present or absent in the molecular image in at least one of the one or more analyses of the molecular image, perform at least one of:
(i) causing transmission to a user of the molecular imaging system of a recommendation that the molecular image acquisition be stopped before a scheduled end of the molecular image acquisition to limit the duration of the molecular image acquisition, and
(ii) causing transmission of a signal to the molecular imaging system to stop the image acquisition automatically before a scheduled end of the image acquisition to limit the time of image acquisition.

14. The system of claim 13 wherein a maximum duration or a maximum number of counts of the image acquisition is set at or before the beginning of the image acquisition, and the at least one of the one or more software algorithms is configured, after determining that at least one area indicative of a lesion is present or absent in the molecular image, to perform at least one of:
(i) causing transmission of the recommendation that the image acquisition be stopped to a user of the imaging system before an end of the maximum duration or accumulation of the maximum number of counts of the image acquisition, and
(ii) causing transmission of a signal to the imaging system to stop the image acquisition automatically before the end of the maximum duration or accumulation of the maximum number of counts of the image acquisition.

15. The system of claim 13 wherein the one or more software algorithms comprise one or more artificial intelligence algorithms.

16. The system of claim 13 wherein the one or more software algorithms comprise at least one of a machine learning algorithm, a deep learning algorithm, a pattern recognition algorithm, an image segmentation algorithm, a signal-preserving noise filtering algorithm, or a count-density contouring algorithm.

17. The system of claim 13 wherein a time during the image acquisition to initiate a first of the one or more analyses of the molecular image is input and one or more periods of time between consecutive analyses is input.

18. The system of claim 13 further comprising a data communication system to receive data of the molecular image from the molecular imaging system.

19. The system of claim 18 wherein the molecular imaging system comprises a molecular breast imaging (MBI) system, a single photon emission (SPE) planar imaging system, a single photon emission computed tomography (SPECT) system, or a positron emission tomography (PET) system.

20. The system of claim 13 further comprising another software algorithm, to measure a characteristic of at least one of (a) a background parenchyma or (b) the at least one area indicative of a lesion, and to assess a diagnostic significance of the at least one area indicative of a lesion via comparison to an established lexicon.

21. The system of claim 20 wherein the characteristic of the background parenchyma is a standardized uptake value of the background parenchyma, and wherein the characteristic of the at least one area indicative of a lesion is selected from the group consisting of a standardized uptake value of the at least one area indicative of a lesion, a size of the at least one area indicative of a lesion, and a location of the at least one area indicative of a lesion.

* * * * *